United States Patent [19]
Novack

[11] 3,954,482
[45] May 4, 1976

[54] CORROSION RESISTANT COATING MATERIAL AND METHOD

[75] Inventor: Robert Lee Novack, Medfield, Mass.

[73] Assignee: High Performance Coatings, Inc., Newton Highlands, Mass.

[22] Filed: May 24, 1973

[21] Appl. No.: 363,613

[52] U.S. Cl. ..................... 106/1; 106/14; 106/84; 106/193 M; 260/37 M; 260/37 EP; 260/37 SB; 260/40 R; 260/42.22
[51] Int. Cl.² .......................................... C09D 5/10
[58] Field of Search ............... 106/1, 14, 193 M, 84; 260/37 M, 39 M, 41 B, 42.22, 37 EP, 37 SB, 40 R

[56] References Cited
UNITED STATES PATENTS

| | | | |
|---|---|---|---|
| 2,716,614 | 8/1955 | O'Connell | 106/193 M |
| 2,718,506 | 9/1955 | Elleman | 260/37 M |
| 3,392,036 | 7/1968 | McLeod | 106/1 |
| 3,764,067 | 10/1973 | Coffey | 260/37 M |

*Primary Examiner*—Lorenzo B. Hayes
*Attorney, Agent, or Firm*—Rines and Rines

[57] ABSTRACT

This disclosure deals with a novel corrosion-resistant primer or other coating material that has been found to become far more efficacious through the appropriate addition of stainless steel planar flakes of rather critical geometry, dimensions and proportions.

11 Claims, No Drawings

CORROSION RESISTANT COATING MATERIAL AND METHOD

The present invention relates to corrosion-resistant coating materials such as primers and the like and to methods of preparing the same, being more particularly concerned with increasing the anti-corrosive effect of those primers or other coatings having electrochemically active metal film additives and/or oxygen and moisture diffusion barrier additives.

Though the present invention will be described in connection with the illustrative example of primer coatings, it is to be understood that the invention is applicable in the coating field generally, wherever the same phenomena are desired; and, more particularly, in the area of anti-corrosion coating. For many years organic and inorganic primers have been used, for example, in the painting of metal and the like for several functions or purposes, including (1) a base for a final top coat, (2) an anti-corrosive layer resistant to atmospheric pollution, (3) bonding to substrates, and (4) for film strengthening. In connection with anti-corrosive applications, the attack by oxygen and moisture often causes rusting of exposed metal surfaces. Atmospheric pollution containing sulphur dioxide and other gases similarly attacks exposed surfaces. While it is the function of an effective anti-corrosive primer to upgrade the protection by the coating to such vapors or conditions, the fact is that the problem of long life for such protective coatings still exists in the art and is still the subject of much research and development activity in view of the importance and high cost involved.

As described, for example, in Metal Finishing Guidebook Directory, published by Metals and Plastics Publications, Inc., Westwood, N. J. 1972, commencing with p. 586, there has been prior usage of electrochemically active anti-corrosive additives, such as zinc dust or other elemental zinc in high concentration; and also zinc chromate (sometimes known) as zinc yellow), the higher lead oxides such as so-called red lead, and basic lead silico-chromates. These types of anti-corrosive additives may be used in high concentration to provide a protective surface that prevents attack of the metal or other surface on which the coating is applied. Some of the above additives and others, such as red iron oxide, operate significantly as oxygen and moisture diffusion barriers that provide some protection to the underlying metal or other surface. Current trends have limited the uses of some of these materials, particularly those involving lead, however, as possible health hazards. Unfortunately, moreover, bridges and other outdoor structures, particularly those in ocean and related environments, subject to salt spray or other serious atmospheric and environmental abuse, have to be scraped and repainted every few years at great expense and inconvenience despite the use of such primers as undercoats.

Numerous approaches have been tried and are still being tried to improve this situation and better solve this problem, including upgrading the paint materials with alkyd epoxy, chlorinated rubber, silicone, vinyl and polyurethane resins and the like; but these have not adequately solved the problem. As described in an article entitled "Stainless Steel Paints", appearing in Metal Finishing, February, 1967, commencing with page 62, it has been suggested that the anti-corrosive pigments of corrosion inhibitive primers might be combined with conventional stainless steel particle pigments, such as those marketed under the trademark "Stay-Steel" by Chas. Pfizer & Co., into a one-coat primer top coat that might offer stainless steel reinforcement. In practice, however, it has not been found that such a proposal, with conventional stainless steel particles so admixed into a single coat, has actually served significantly to improve the situation. The above-mentioned article points out that such a single coat proposal had not heretofore in practice been able fully to achieve the desired results.

Underlying the present invention, however, is the unexpected discovery that, if stainless steel particles are rather critically geometically reshaped and dimensioned, and appropriately admixed, they can indeed be dispersed in anti-corrosive primer binders as a single coat, with a rather remarkable synergistically obtained improved protection performance.

The present invention, therefore, has as one of its primary objectives the provision of a new and improved corrosion resistant coating material that employs such critically dimensioned stainless steel material, and improved methods of preparing the same, greatly to improve the protective characteristics of a single coating and the-like.

A further object is to provide a new and improved corrosion resistant primer.

Other and further objects will be explained hereinafter and are more particularly delineated in the appended claims.

In summary, however, from one of its important aspects, the invention contemplates a corrosion-resistant material comprising a primer binder containing dispersed therethrough stainless steel planar flakes of thicknesses of the order of several tenths of a micron and of surface dimensions largely of the order of 10 to 40 microns, and preferably in a quantity of the order of at least one pound of stainless steel flakes per gallon of primer. Preferred details are hereinafter presented.

As above stated, it has been quite accidentally discovered that the use of stainless steel particles in extremely thin planar flake form, as distinguished from the arbitrary shape, somewhat spherical or other discreet particle size, as in the prior art stainless steel pigments, including those before-mentioned, vastly improves the protective quality of primer binders and similar coatings in a manner that cannot be attained with stainless steel particles of the shapes and sizes previously used.

When such prior art stainless steel pigments are added to conventional red primers containing zinc chromate, zinc oxide and red iron oxide, for example, and the same is applied as a primer to steel surfaces and exposed to rigid salt spray attack over prolonged periods of time, the coating has been found seriously to blister and rust to about the same degree as the primer alone without the added stainless steel particles. When, however, the same amount of stainless steel was added to and dispersed in the primer in exactly the same conditions of test, but with the stainless steel in the form of planar flakes of the above-mentioned rather critical dimensions and configuration, vastly improved, and indeed in some cases, negligible blistering and rusting results were obtained.

Specifically, using the before-mentioned anti-rust primer of the type marketed by Sears under No. 68592 (pigment 49.7% including zinc chromate 24.9%, zinc oxide 16.6%, red iron oxide 24.9%, magnesium silicate 24.9%, white cement 8.3%, aluminum stearate .4%;

and vehicle 50.3% including soya alkyd resin 41.8%, mineral spirits and driers 58.2%), with 1 pound of the said "Stay-Steel" stainless steel pigment per gallon of primer, salt spray testing was conducted on steel plates in accordance with ASTM Test Bi, B117 (100°F at 5% salt spray). This same test was performed with exactly the same weight of stainless steel flakes having an average thickness of 0.34 or ⅓ micron and surface dimensions of the flakes largely in the range of from 10–40 microns (with approximately 33% being in the range of 20–30 microns, about 14% from 30–40 microns and about 30% between 10 and 20 microns), with the surface dimensions of the flakes being very large compared to the minute thickness of the flakes. Additionally, the same test was performed with the anti-corrosive primer alone absent of any type of stainless steel additive.

On a scale of 10 established by the said test, after 140 hours of salt spray exposure, the plates coated with the primer alone and with the primer and "Stay-Steel" particles showed the same degradation as follows: blistering down to 7; and rusting down to 5. In connection with the primer containing the stainless steel planar flakes, however, the blistering was extremely slight, at 9; and the rusting was also slight, at 8. After 290 hours of the salt spray exposure, the plates with the primer alone showed a degradation of blistering to 5, and a rusting down to 3; being somewhat better than the primer with the "Stay-Steel" particles, which degraded to a blistering of 4 and a rusting of 3. The 290 hour test with the before-mentioned stainless steel planar flakes additive, however, still showed but slight blistering at 8, and very slight degradation in rusting at 7.

Other salt spray tests with zinc chromate primer similarly showed remarkably improved rust inhibiting performance in accordance with the invention.

It was further found that while improved results could be obtained within a rather wide range of variation of stainless steel flake additive proportions, if the weight were reduced substantially below one pound of stainless steel additive per U.S. gallon of primer, the results were closer to the performance of the primer alone; such that at least of the order of approximately one pound of stainless steel flakes additive per gallon of primer has been determined to be desirable for the more spectacular improvement results above delineated.

While there is no intention to be bound by theoretical explanations, correct or incorrect, it being sufficient merely to describe the construction that has been found to work in practice, it may be helpful to consider what is believed to be a possible explanation for this unexpected improved result. In the case of anti-corrosive primer additives of the type that form metallic film (such as elemental zinc additives before-mentioned and the like), it appears that those particles that contact the stainless steel flakes have a vastly improved or enhanced electrochemical reaction beyond that attainable with the metallic film alone in the absence of said flakes, such that a more effective protective surface is thereby attained. This, of course, is supplemental to the inherent protection provided by the surface formed by the planar flakes of stainless steel. In connection, moreover, with anti-corrosive additives (such as iron oxide, lead oxide and the like), which appear to protect at least in part as a result of forming an oxygen and moisture diffusion barrier, the contacting of the same with the stainless steel flake barrier appears to provide a supplemental and vastly improved diffusion barrier effect, with the barriers cohering in improved fashion.

A second example of efficacious use of the invention is the use of substantially one pound of the said critically dimensioned stainless steel planar flakes in a gallon of Irco zinc chromate primer in an organic binder, where no evidence of rust even started to appear until slightly over 300 hours of intense salt spray testing.

As a further example, the successful tests first described in connection with the Sears primer and its anti-corrosive zinc chromate, zinc oxide and red iron oxide additives were conducted with the stainless steel planar flakes of the critical shape and dimensions before detailed dispersed in the organic primer binder after the flakes had been formed with mineral spirits into a paste. The paste was mixed rapidly into the binder containing the anti-corrosive elements above mentioned.

As still another example, the primer organic binder with which the said stainless steel flakes are mixed may comprise a binder material selected from the group consisting of alkyd, epoxy, vinyl, silicone, chlorinated rubber, and polyurethane resins.

As still a further illustration, the binder receiving the stainless steel flakes may be inorganic, as of zinc alkali silicates.

As other examples, in addition to the elemental zinc, zinc chromate and zinc oxide pigment additives for anti-corrosion purposes, where health hazard restrictions are not applicable, lead oxide and lead silicochromate may be used, as well as combinations of all of the above with the flakes.

As still another example, diffusion barrier supplementation with the said stainless steel flakes may be attained with iron oxide and lead oxide additives.

In all of the above cases, the conventional electrochemically active anti-corrosion metal film additives and/or the diffusion barrier additives were employed in precisely the conventional commercial proportions that have been used for many years and are currently used in the conventional organic and inorganic primer binders, such as the specific examples above referenced.

As before stated, while the invention is particularly efficacious in its application to a one-coat anti-corrosive stainless steel additive coating, it is clearly applicable with other coatings wherein the improvement herein attained may be desired. It should be noted that the invention in no way modifies the physical and other properties of the primer or other coating so that paint or other treatment may be applied as in present-day operation. Further modifications will occur to those skilled in this art and all such are considered to fall within the spirit and scope of the invention as defined in the appended claims.

What is claimed is:

1. In a corrosion-resistant coating composition comprising a primer selected from the group consisting of organic and inorganic binders and metallic particles dispersed therethrough; the improvement comprising, as said particles, stainless steel planar flakes of thickness of the order of ⅓ of a micron and of surface dimensions largely of the order of 10 to 40 microns and in amounts of at least 1 pound per gallon of primer.

2. A corrosion-resistant coating composition as claimed in claim 1 and in which said primer further contains an anti-corrosive additive for forming a metallic film that contacts said flakes and, by electrochemical action, forms a protective surface additonal to that formed by the said planar flakes, the contact between the said film and flakes enhancing said electrochemical action beyond that attainable with the additive alone in the absence of said flakes.

3. A corrosion-resistant coating composition as claimed in claim 2 and in which said additive is selected from the group consisting of elemental zinc, zinc chromate, zinc oxide, lead oxide, lead silico-chromate, and combinations thereof.

4. A corrosion-resistant coating composition as claimed in claim 1 and in which said primer further contains an anti-corrosive additive for forming an oxygen and moisture diffusion barrier that contacts said flakes and supplements the barrier effect of said planar flakes.

5. A corrosion-resistant coating composition as claimed in claim 4 and in which said additive is selected from the group consisting of iron oxide and lead oxide.

6. A corrosion-resistant coating composition as claimed in claim 1 and in which said primer binder comprises an organic resin.

7. A corrosion-resistant coating composition as claimed in claim 6 and in which said primer binder is selected from the group consisting of alkyd, epoxy, vinyl, silicone, chlorinated rubber and polyurethane resins.

8. A corrosion-resistant coating composition as claimed in claim 1 and in which said primer binder comprises zinc-alkali silicates.

9. A corrosion-resistant coating composition as claimed in claim 1 and in which said flakes are initially formed as a paste in mineral spirits prior to dispersion in the primer binder.

10. In a method of increasing the corrosion-resistant effect of anti-corrosive primer resins containing at least one of electrochemically active metal film additives and oxygen moisture diffusion barriers; the improvement comprising adding to the primer resin stainless steel planar flakes in amounts of at least one pound per gallon of primer resin, said flakes having a thickness of the order of ⅛ of a micron and surface dimensions largely of the order of 10 to 40 microns, and dispersing said flakes through the primer resin to provide a supplemental protective surface that cooperates with such metal film additives to increase the electrochemical protection thereof and cooperates with said diffusion barriers to provide a supplemental flake barrier.

11. A method as claimed in claim 10 and in which said stainless steel flakes are added in the form of a mineral spirits paste.

* * * * *